United States Patent
Kugel (12)

(10) Patent No.: US 6,224,616 B1
(45) Date of Patent: *May 1, 2001

(54) HERNIA MESH PATCH (75) Inventor: Robert D. Kugel, Olympia, WA (US)

(73) Assignee: Bard ASDI Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/304,365

(22) Filed: May 4, 1999

Related U.S. Application Data (63) Continuation of application No. 09/006,653, filed on Jan. 14, 1998, now Pat. No. 5,916,225, which is a continuation of application No. 08/755,108, filed on Nov. 22, 1996, now Pat. No. 5,769,864, which is a continuation-in-part of application No. 08/315,249, filed on Sep. 29, 1994, now Pat. No. 5,634,931.

(51) Int. Cl.[7] .................................................. A61B 17/04
(52) U.S. Cl. ........................... 606/151; 128/898; 602/44; 602/58
(58) Field of Search ........................... 606/151, 213–215; 128/898

(56) References Cited

U.S. PATENT DOCUMENTS

| | | | |
|---|---|---|---|
| 2,671,444 | 3/1954 | Pease, Jr. | 606/151 |
| 3,054,406 | 9/1962 | Usher | 606/151 |
| 4,007,743 | 2/1977 | Blake . | |
| 4,347,847 | 9/1982 | Usher | 606/151 |
| 4,452,245 | 6/1984 | Usher | 606/151 |
| 4,561,434 | 12/1985 | Taylor . | |
| 4,633,873 | 1/1987 | Dumican et al. | 606/151 |
| 4,655,221 | 4/1987 | Devereux . | |
| 4,693,720 | 9/1987 | Scharnberg et al. . | |
| 4,710,192 | 12/1987 | Liotta et al. . | |
| 4,769,038 | 9/1988 | Bendavid . | |

(List continued on next page.)

FOREIGN PATENT DOCUMENTS

| | | |
|---|---|---|
| 2114282 | 7/1994 | (CA) . |
| 0 362 113 | 4/1990 | (EP) . |
| 0 474 887 | 10/1991 | (EP) . |
| 676 285 | 7/1979 | (SU) . |
| 782 814 | 11/1980 | (SU) . |
| WO 90/14796 | 12/1990 | (WO) . |
| WO 93/17635 | 9/1993 | (WO) . |
| WO 94/27535 | 12/1994 | (WO) . |
| WO 96/09795 | 4/1996 | (WO) . |
| WO 97/22310 | 6/1997 | (WO) . |

OTHER PUBLICATIONS

Declaration by Inventor of Prior Work.

(List continued on next page.)

Primary Examiner—Gary Jackson
(74) Attorney, Agent, or Firm—Wolf, Greenfield & Sacks, P.C.

(57) ABSTRACT

A method for repairing a hernia uses a mesh patch for permanent placement within a patient's body space. The patch has top and bottom mesh layers secured to each other with a seam. The seam surrounds and defines a pocket. The top layer has a transverse slit opening into the pocket. To serve a spring function, an implantable loop is inserted into the pocket to keep the patch expanded under tension in a planar configuration. A border on at least one of the layers extends outward past the seam. The border preferably has slits to fill uneven voids in the patient's tissue and fit more tightly. A surgeon makes a small incision in the patient and performs a dissection deep into the patient's preperitoneal space, creating a pocket in this space into which the patch is to be inserted. The patch is folded and directed into the patient's preperitoneal space, where it is unfolded and expanded into its planar configuration to cover the defect in the patient. Thereafter the surgeon secures the incision with stitches.

58 Claims, 3 Drawing Sheets

U.S. PATENT DOCUMENTS

| | | |
|---|---|---|
| 4,796,603 | 1/1989 | Dahlke . |
| 4,854,316 | 8/1989 | Davis . |
| 4,865,026 | 9/1989 | Barrett . |
| 4,955,907 | 9/1990 | Ledergerber . |
| 5,006,106 | 4/1991 | Angelchik . |
| 5,059,205 | 10/1991 | El-Nounou et al. . |
| 5,116,357 | 5/1992 | Eberbach .......................... 606/151 |
| 5,122,155 | 6/1992 | Eberbach .......................... 606/151 |
| 5,141,515 | 8/1992 | Eberbach .......................... 606/151 |
| 5,147,374 | 9/1992 | Fernandez ......................... 606/151 |
| 5,147,384 | 9/1992 | La Rocca . |
| 5,147,387 | 9/1992 | Jansen . |
| 5,176,692 | 1/1993 | Wilk et al. . |
| 5,192,301 | 3/1993 | Kamiya et al. . |
| 5,195,542 | 3/1993 | Gazielly et al. . |
| 5,201,745 | 4/1993 | Tayot et al. . |
| 5,254,133 | 10/1993 | Seid . |
| 5,258,000 | 11/1993 | Gianturco . |
| 5,290,217 | 3/1994 | Campos . |
| 5,318,559 | 6/1994 | Mulhauser . |
| 5,334,217 | 8/1994 | Das . |
| 5,350,399 | 9/1994 | Erlebacher et al. ............... 606/151 |
| 5,356,432 | 10/1994 | Rutkow et al. . |
| 5,366,460 | 11/1994 | Eberbach .......................... 606/151 |
| 5,368,602 | 11/1994 | de la Torre ....................... 606/151 |
| 5,370,650 | 12/1994 | Tovey et al. . |
| 5,397,331 | 3/1995 | Himpens et al. . |
| 5,425,744 | 6/1995 | Fagan et al. . |
| 5,433,996 | 7/1995 | Kranzler et al. . |
| 5,451,235 | 9/1995 | Lock et al. . |
| 5,456,720 | 10/1995 | Schultz et al. . |
| 5,507,811 | 4/1996 | Koike et al. . |
| 5,593,441 | 1/1997 | Lichtenstein et al. . |
| 5,614,284 | 3/1997 | Kranzler et al. . |
| 5,695,525 | 12/1997 | Mulhauser et al. . |
| 5,702,416 | 12/1997 | Kieturakis et al. . |
| 5,716,408 | 2/1998 | Eldridge et al. . |
| 5,743,917 | 4/1998 | Saxon . |
| 5,766,246 | 6/1998 | Mulhauser et al. . |
| 5,769,864 | 6/1998 | Kugel ................................ 606/151 |
| 5,824,082 | 10/1998 | Brown . |
| 5,836,961 | 11/1998 | Kieturakis et al. . |
| 5,879,366 | 3/1999 | Shaw et al. . |
| 5,916,225 | 6/1999 | Kugel . |
| 5,919,232 | 7/1999 | Chaffringeon et al. . |
| 5,922,026 | 7/1999 | Chin . |
| 5,954,767 | 9/1999 | Pajotin et al. . |

OTHER PUBLICATIONS

"Minimally Invasive, Non–Laparoscopic, Preperitoneal, Sutureless, Iguinal Herniorrhaphy" by Robert D. Kugel (not published). See Exhibit 2 of Declaration.

Gregory L. Brown, M.D. et al., "Comparison of Prosthetic Materials for Abdominal Wall Reconstruction in the Presence of Contamination and Infection", Annals of Surgery, Jun. 1985, vol 201, pp. 705–711.

Scott D. Jenkins, M.D. et al., "A Comparison of Prosthetic Materials Used to Repair Abdominal Wall Defects", Surgery, Aug. 1983, vol. 94, No. 2, pp. 392–398.

"Prevention of Postsurgical Adhesions by Interceed (TC7)", Fertility and Sterility, Jun. 1989, vol. 51, No. 6, pp. 933–938.

Hernando Cordona, M.D., "Prosthokeratoplasty", 1983, Cornea, vol. 2, No. 3, 1983, pp. 179–183.

Alonzo P. Walker, M.D., et al., "Double–Layer Prostheses for Repair of Abdominal Wall Defects in a Rabbit Model", pp 32–37, Journal of Surgical Research, vol. 55, No. No. 1, Jul. 1993.

HERNIA MESH PATCH

This application is a continuation of application Ser. No. 09/006,653, filed Jan. 14, 1998, entitled Hernia Mesh Patch now U.S. Pat. No. 5,916,225, which was a continuation of application Ser. No. 08/755,108, filed Nov. 22, 1996, entitled Hernia Mesh Patch, issued as U.S. Pat. No. 5,769,864, which was a continuation-in-part of application Ser. No. 08/315,249, filed Sep. 29, 1994, entitled Hernia Mesh Patches and Methods of Their Use, issued as U.S. Pat. No. 5,634,931, on Jun. 3, 1997.

TECHNICAL FIELD

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of these earlier techniques are somewhat complicated. Several use a plug or a locating member to fit within the hernia defect itself. Also many of these earlier techniques were designed specifically for use in laparoscopic repair of hernias. Moreover, many of the prior inventions required suturing to the patient's body tissue. Although these medical advances are acknowledged for their usefulness and success, there remained a need or needs for more improvements in the surgical repair of hernias.

DISCLOSURE OF INVENTION

A hernia mesh patch for use in the surgical repair of a patient's inguinal, or other abdominal wall hernias, is disclosed for permanent placement within a patient's body space. This hernia mesh patch has top and bottom layers of an inert, synthetic mesh, preferably polypropylene mesh, secured to each other with a seam. The seam surrounds and defines a pocket. The top layer has a transverse cut or slit opening into the interior pocket or pouch volume of this patch.

To serve a spring function, an implantable inert monofilament fiber, arranged in an oval, ovoid, loop, or ring configuration, having a circumference slightly greater than the circumference of the interior pocket volume of this patch, is inserted into this pocket to keep the hernia mesh patch expanded under tension in a planar configuration. A border on at least one of the layers extends outward past the seam. The border preferably has slits to fill uneven voids in the patient's tissue and fit more tightly.

Without the need for general anesthesia, nor expensive laparoscopic instrumentation, a surgeon, when repairing an inguinal hernia, makes a small incision in the patient, approximately three centimeters long, arranged obliquely, approximately two to three centimeters above the internal ring location of the inguinal hernia. Through this small incision, using the muscle splitting technique, the surgeon performs a dissection deep into the patient's properitoneal space, creating a pocket in this space into which this hernia mesh patch is to be inserted.

Thereafter, the surgeon, using his or her fingers, readily folds and compacts this hernia mesh patch and directs it through the incision and into the patient's properitoneal space, where it unfolds and expands into its planar configuration, creating a trampoline effect. Then the surgeon, using just one of his or her fingers, placed partially through a slit in the top layer of mesh and into the pocket between the top and bottom layers of this hernia mesh patch, conveniently and accurately moves the hernia mesh patch to cover the defect in the patient's thick reinforcing lining of his or her abdominal cavity. Thereafter the surgeon withdraws his or her finger and then secures the incision with stitches.

The patient's body, soon after surgery, reacts to the mesh of the hernia mesh patch, and in a short time, the mesh becomes stuck, thereby keeping the hernia mesh patch in place. Thereafter the patient's scar tissue grows into the mesh over a period of time, between thirty and sixty days, to permanently fix the hernia mesh patch in its intended position over the repaired area, where the hernia was located.

In respective designs of these hernia mesh patches, small holes are cut through both layers of the mesh inside the fiber ring, to increase friction and to minimize the sliding or migration of the hernia mesh patch, after it is positioned. Also in some designs, spaced spikes are attached to the fiber spring, or are integrally formed with the fiber spring to serve as anchors, by entering the patient's tissue. Also in some designs of these hernia mesh patches to be used in a location where the patient's peritoneum has been destroyed, one layer of this patient's hernia patch is made of a material, such as "Gortex" material, which is less prone to adhere to a bowel or other intra-abdominal organ.

BEST MODE FOR CARRYING OUT THE INVENTION

Figures 1, 2:
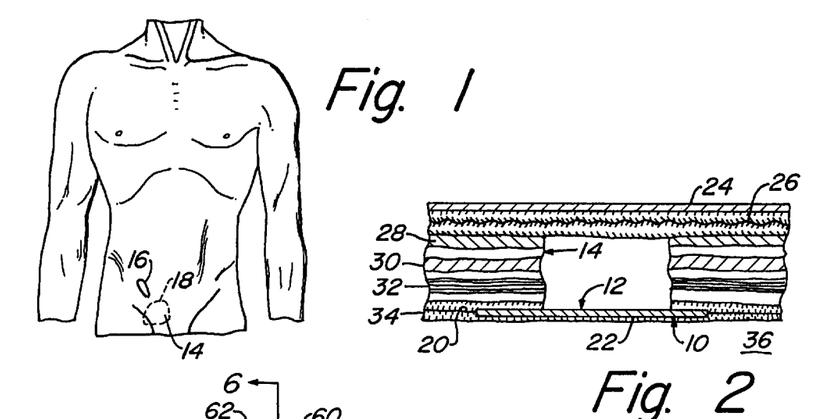
FIG. 1 is a schematic partial front view of a patient's body indicating, in respect to the surgical repair of an inguinal hernia, where a three centimeter incision is made obliquely approximately two to three centimeters above the location described as the internal ring of the hernia, in reference to the location of an inguinal hernia.
FIG. 2 is a schematic partial diagrammatic cross-sectional view of a patient's abdominal wall layers showing an inguinal or other abdominal wall hernia, and where the surgically implantable hernia repair mesh patch has been correctly positioned in the properitoneal created space.

The hernia mesh patches 10, illustrated in the drawings, are surgically permanently implantable within a patient's body space 12 to adequately cover, correct, prevent and repair any inguinal or other abdominal wall hernias 14 or other types of hernias. The surgeon has the objective of making a sutureless repair, by first cutting an approximately three centimeter incision 16, obliquely positioned approximately two to three centimeters above the location described as the internal ring 18, where an inguinal hernia 14 has occurred, as shown in FIG. 1. Then the surgeon working through this incision 16, and using a muscle splitting technique, dissects deeply into the patient's properitoneal space 20, entering slightly superior and posterior to the patient's hernia defect 14. The surgeon then creates a pocket 22 in the patient's properitoneal space 20, into which the hernia mesh patch 10 is inserted, as shown in FIG. 2.

The surgeon in dissecting deeply into the patient's properitoneal space 20, as indicated in FIG. 2, will have used a sharp instrument to make the incision or wound 16 through the patient's skin 24, the subcutaneous fatty tissues 26, and the external oblique fascia 28, which has been cut parallel with its fibers a short distance. Then the surgeon has incised the transversalis fascia 32, creating an entrance into the properitoneal space 20, above the peritoneum 34 at a location superior to the hernia 14. In so doing, the surgeon has identified and freed up the hernia sac and has created the pocket 22 in the properitoneal space 20. This space 20 underlies the area referred to as Hesselbach's triangle, in reference to both indirect and direct hernias. The surgeon's placement of this hernia mesh patch 10, using this method, protects the entire inguinal floor, and therefore not only will it repair or correct a single small hernia, but will also protect against future hernias through other potentially weakened areas. In a similar way, a hernia mesh patch 10, sandwiched between a hernia 14, i.e. defect 14, and the inner lining 34, i.e. the peritoneum 34, of the abdominal cavity 36, is used to underlay a femoral canal area, not shown, through which femoral hernias occasionally occur. Wherever used, the hernia mesh patch 10, in its respective embodiments, serves as the basis for tension free surgical repair of a hernia, as it is used to patch and to bridge the hernia 14, i.e. the defect 14. The hernia mesh patch 10 is made, so after completing this preparation, the surgeon using his or her fingers, can fold and compact the hernia mesh patch 10 and insert it down through the incision 16 into properitoneal space 20. Thereafter, using his or her finger, the surgeon expands, moves, and directs, the hernia mesh patch 10 into position in the pocket 20 within the properitoneal space 20 to bridge the hernia 14, or defect 14.

An embodiment 40 of these hernia mesh patches 10, is illustrated in FIGS. 2 through 6, which is particularly designed for the repair of an inguinal hernia 10 but also can be used for other abdominal wall hernias. This embodiment 40 is composed of two similarly sized and shaped pieces 42, 44, of an inert synthetic mesh material 46, which preferably is a polypropylene material. This mesh material 46 is formed from monofilament material which is resistant to infection, and which has been used safely in many hernia operations, in previous ways and in previous embodiments. Preferably, the two similarly sized and shaped pieces of mesh material 42, 44 are made in respective circle, loop, ovoid, or oval shapes. One of these pieces 42, 44, is referred to as the first or top layer 42 of the synthetic mesh material 46 and the other one of these pieces 42, 44, is referred to as the second or bottom layer 44 of the synthetic mesh material 46. These two layers 42, 44, are secured to each other by sewing in the first three embodiments and by sonic welding in the last embodiment. In the first three embodiments, the seam is approximately one centimeter in from their outer edges 48, 50 using a thread 51 of inert synthetic material. The outer one centimeter of mesh material 52 of the bottom mesh material piece or layer 44 is left free to serve as a border or apron 54 to fill uneven voids in the patient's tissue. The outer one centimeter of mesh material 52 of the top mesh material piece or layer 42 is folded back and sewn adjacent the fold 56, while leaving free the remaining portions of this outer one centimeter of mesh material 52 of this top mesh layer 42. Thereafter, this free portion 57, when the hernia mesh patch 10 has been placed in the properitoneal space, serves to frictionally keep this patch 10 in its hernia 14 repair position. Also inside of the fold 56, like size holes 59, aligned one above the other, are cut respectively in the top and bottom mesh layers 42, 44. The presence of these holes 59 helps initially to frictionally keep the hernia mesh patch 10 in place. Thereafter the patient's scar tissues grow in and around these holes 59 to continue to keep the hernia mesh patch in position. The outer one centimeter of mesh materials 52 are both cut or slit 58, radially or diagonally creating scalloped or fringed edges 60, or tab portions 62, of both the outer one centimeter of mesh materials 52, of the top and bottom mesh layers 42, 44.

Figure 3:
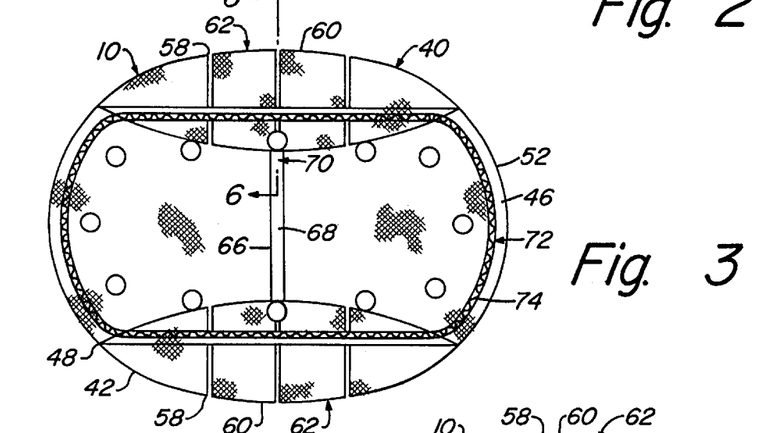
FIG. 3 is a top view of a preferred embodiment of the surgically implantable hernia repair mesh patch, having anchoring or friction holes cut through both layers of the mesh, which after the surgical insertion of the surgically implantable hernia repair mesh patch, serve to minimize any risk of the mesh migrating or moving once positioned by a surgeon.
Figure 4:
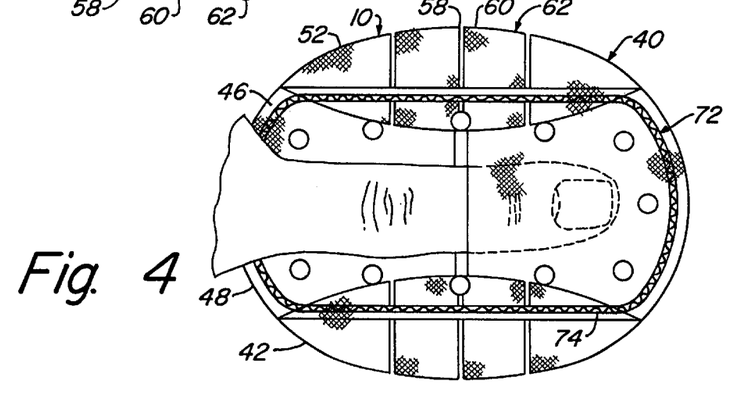
FIG. 4 is similar to FIG. 3, showing how a surgeon's finger is inserted through a slit, which is made by cutting through only the top layer of the two layers of mesh used in this surgical hernia patch, whereby a surgeon's finger, so inserted between these layers of mesh, then directs the movement of this surgical hernia patch through the incision and on to the location of the inguinal hernia.

Also the top mesh material, or top layer piece 42, is cut or slit 66 transversely at the center 68 thereof, creating a finger access 66 into the interior space 70, or pouch 70, between the top and bottom layers 42, 44 of the synthetic mesh material 46. Through this slit 66, a ring like arrangement 72 of a continuous, inert, implantable, monofilament fiber 74, when squeezed temporarily to narrow it and to elongate it, is inserted into the interior space 70 or pouch 70. Then it is released, and allowed to expand, serving a spring function and therefore it is called a spring 72, while it is compressibly held in this interior space 70 or pouch 70 of the hernia mesh patch 10, thereby keeping this patch 10 fully extended in a planar arrangement, as shown in FIGS. 2, 3, and 4. This spring 72 is made of a synthetic material, such as nylon, polypropylene, or polyester. In each embodiment, this monofilament loop, ring or spring 72, has a circumference which is slightly larger than the circumference of the interior space 70, or pocket 70, or pouch 70, which is formed between the top and bottom layers 42, 44 of the synthetic mesh material 46.

Figures 5, 6, 7, 8, 9:
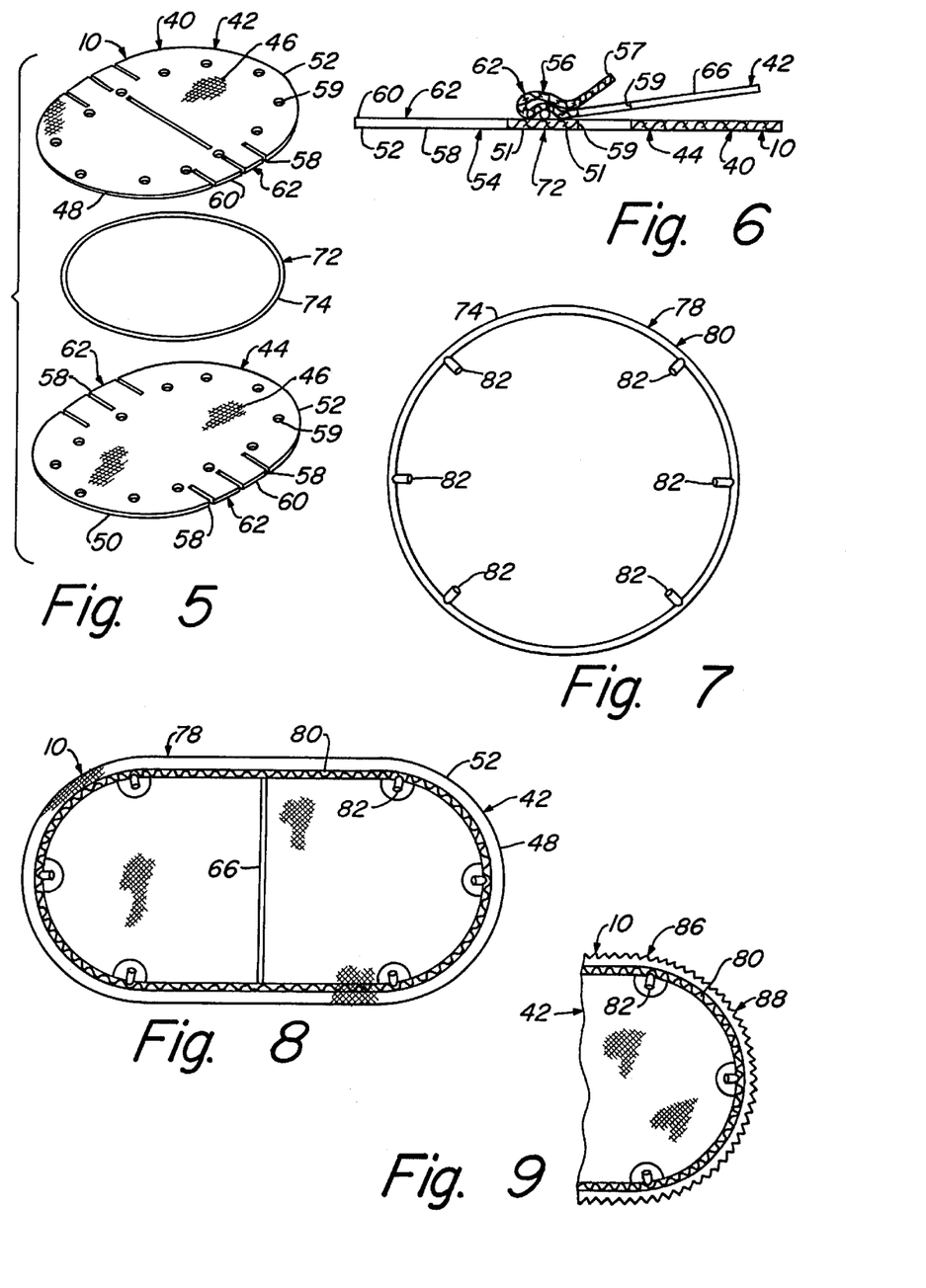
FIG. 5 is an exploded view of the surgically hernia repair mesh patch shown in FIGS. 2, 3 and 4, to show the two layers of the mesh, preferably cut from polypropylene mesh material, and also to show a resilient monofilament ring, which when located between the layers of mesh, becomes a resilient spring ring keeping the surgical hernia patch fully expanded.
FIG. 6 is a transverse cross sectional view of the center of the preferred surgically implantable hernia repair mesh patch, illustrated in FIGS. 2, 3, 4 and 5, with the top and bottom layers shown slightly separated for illustrative purpose.
FIG. 7 is a top view of another resilient monofilament ring, which becomes the located spring ring, showing how spaced anchoring monofilament spikes are secured to this ring or are made integral with this ring or are made integral with this ring.
FIG. 8 is a top view of a second embodiment of the surgically implantable hernia repair mesh patch.
FIG. 9 is a partial top view of a third embodiment illustrating a circular surgically implantable hernia repair mesh patch.

A second embodiment 78 is illustrated in FIGS. 7 and 8, wherein the ring or spring 80 has spaced monofilament spikes 82 secured to the ring 80, or made integrally with it. They are directed on an angle to extend above this embodiment 78 of a hernia mesh patch 10, to enter the patient's body tissue. In this way the continuing accurate location of this hernia mesh patch 10 is insured. The outer one centimeter of mesh material 52, as shown in FIG. 8, is not cut nor slit.

A third embodiment 86 is illustrated in FIG. 9, wherein a portion of it is shown, indicating its similarity to the second embodiment 78, illustrated in FIGS. 7 and 8. However, the outer one centimeter of mesh materials 52 are cut to create scalloped or fringed circumferential edges 88, above and below, which also serve to frictionally hold the hernia mesh patch 10 in place, along with the spikes 82 on the loop, ring or spring 80.

Figure 11:
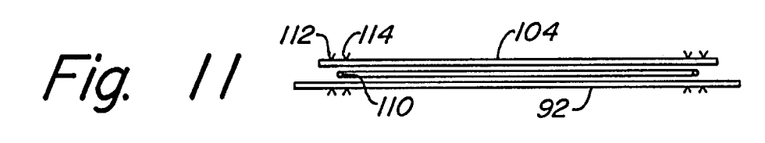
FIG. 11 is a sectional view of the patch of FIG. 10, taken along the line 11—11 of FIG. 10.
Figure 12:
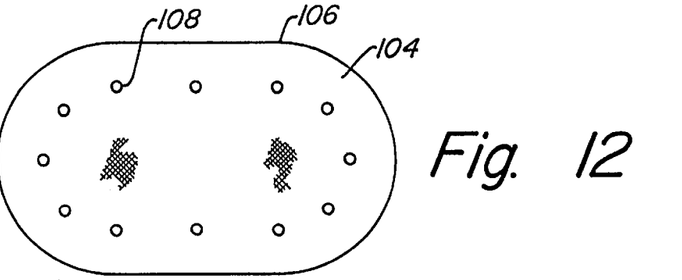
FIG. 12 is a plan view of one of the layers of the patch of FIG. 10.
Figure 13:
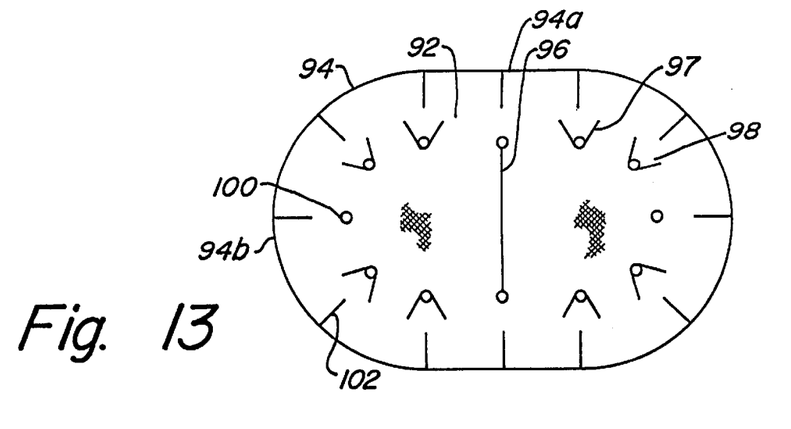
FIG. 13 is a plan view of the other of the layers of the patch of FIG. 10.

A fourth embodiment 90 of a patch 10 is shown in FIGS. 10–13. Patch 90 has a first layer 92 of an inert synthetic mesh material. Layer 92, as shown in FIG. 13, has an outer edge 94 that in the embodiment shown is generally oval, having straight sides 94*a* and curved ends 94*b*. An access slit 96 extends in a straight line transversely across a portion of layer 92, perpendicular to straight sides 94*a*. Slit 96 is large enough to accommodate a finger of a surgeon. In addition, a plurality of dart-shaped slits 97 are formed in layer 92. Dart slits 97 define a dart or triangular shaped tab 98 which pops or protrudes up from layer 92. Dart tabs 98 are oriented in a generally oval array similar to outer edge 94, but spaced inwardly. Four of the dart tabs 98 are located inward from each curved end 94*b*. In addition, a circular hole 100 is located at the center point but inward from each curved end 94*b*.

A plurality of border slits 102 extend inward from each outer edge 94. Each border slit 102 is a straight line. The border slits 102 are located outward from dart tabs 98 and holes 100. In the embodiment shown, there are three border slits 102 leading inward from each straight side 94*a* and three evenly spaced border slits 102 leading inward from each curved end 94*b*.

Figure 10:
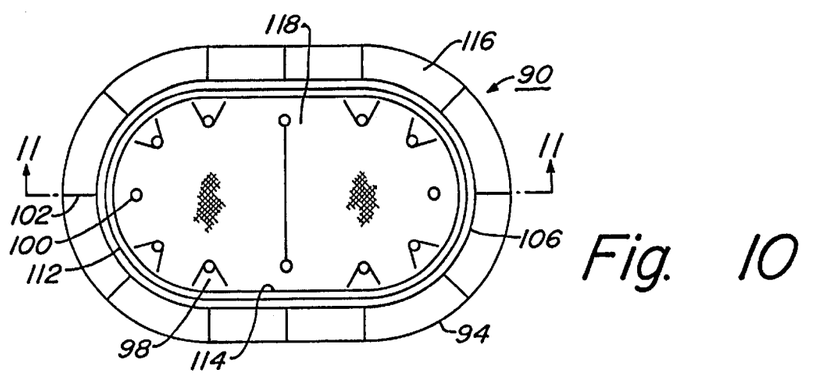
FIG. 10 is a plan view of a fourth embodiment of a patch constructed in accordance with this invention.

Referring to FIG. 12, second layer 104 has a similar oval configuration, however is smaller in size. Second layer 104 is also an inert mesh synthetic material having a generally oval-shaped edge 106. A plurality of holes 108 are located in layer 104. Each hole 108 is circular and spaced in an oval pattern, but inward from outer edge 106. Holes 108 are evenly spaced and aligned with the holes 100 and dart tabs 98 of layer 92 when assembled together as shown in FIG. 10. Dart tabs 98 and holes 100, 108 result in openings extending completely through patch 90.

Referring to FIG. 11, a resilient loop 110 of a monofilament fiber locates between the two layers 92, 104. Once installed, loop 110 is preferably generally oval-shaped. Loop 110 is located outward of holes 108 and slightly inward of outer edge 106 of layer 104. Once assembled as shown in FIG. 11, two seams 112, 114 are formed to join layers 92, 104 together. Seam 114 is located slightly inward of loop 110, while seam 112 is located slightly outward of loop 110. Seams 112, 114 are preferably formed by conventional sonic welding techniques.

Seams 112, 114 are located inward from outer edge 94 of layer 92, creating a border 116. Seams 112, 114 are also located slightly inward of border slits 102. As shown in FIG. 10, seams 112, 114 define a pocket or pouch 118 between layers 92, 104. Access slit 96 serves as access to pouch 118. Loop 110 is located at the perhiphery of pouch 118 and urges patch 90 to a flat configuration. This configuration may be deformed during the insertion and placement of patch 90. Loop 110 causes dart tabs 98 to pop up and protrude from the surface of layer 92. Dart tabs 98 tend to grab tissue when patch 90 is implanted to hold patch 90 in place without the need for sutures.

In use, at the conclusion of the surgeon's use of both sharp and blunt instruments to create pocket 22 in the properitoneal space 20, he or she selects the type and size embodiment of the hernia mesh patch 10 best suited to be used in the repair of the patient's defect or hernia 14. The selected embodiment 40, 78, 86, 90 or another one, not shown, of the hernia mesh patch 10, is folded and further compacted, as may be necessary, by the surgeon using his or her fingers, so the selected patch 10 may be conveniently inserted through the wound or incision 16 and down into the properitoneal space 20. Referring to the first embodiment, shown in FIG. 3, in this space 20, the hernia mesh patch 10 is freed and allowed to expand under the force of the loop 74. Thereafter the surgeon using his or her finger, continues any further expansion of this patch 10, which might be necessary. Then his or her finger is inserted through the cut or slit 66 in the center 68 of the top mesh layer 42, and the hernia mesh patch 10 through the properitoneal space to the pocket 22. After the withdrawal of his or her finger, the surgeon completes the repair surgery by closing the wound or incision with stitches, in respect to this repair of an inguinal hernia, using the remote incision 16, as illustrated in FIG. 1.

In the repair of other hernias, and especially those that are large, a direct incision is made, and after the placement of a large hernia mesh patch 10, the surgeon may use limited sutures to keep the larger hernia mesh patch 10 in place. Generally, most of the embodiments of this hernia mesh patch 10 are positioned, and so remain, without the use of sutures.

In respect to the utilization of all of the embodiments of these hernia mesh patches 10, they have their simplicity of manufacturing design and of their surgical method of insertion. All these patches 10 adequately underlay a hernia 14 or defect 14, with a minimum of two centimeters of a surrounding underlay about the circumference of the hernia 14. They do so, with sufficient rigidity and with sufficient friction, to eliminate or minimize sliding or migration. When these hernia mesh patches 10 are used by a surgeon, the repair of a patient's inguinal hernia 14, or of another abdominal wall hernia 14, is repaired through a smaller wound or incision 16, with less surgical tension, less post-operative patient discomfort, shorter operation time, and at a potential lower cost to the patient.

The hernia mesh patches are made in several sizes. Four standard sizes accommodate ninety percent of the inguinal and abdominal wall hernias. With respect to repairing inguinal hernias, the most appropriate size is eight by twelve centimeters. The diameter of the monofilament fiber, which is preferably made from nylon, polypropylene, or polyester, and arranged to subsequently serve as a spring, is adjusted in size in respect to the selected size of the hernia mesh patch to be used. A larger diameter fiber is used in the spring of a larger diameter mesh patch to make the hernia mesh patch stiffer. While allowing for the sufficient stiffness to insure the hernia mesh patch will open to its predetermined overall dimensions, there must be adequate flexibility to allow this hernia mesh patch to conform to the patient's uneven body contours and surfaces, and initially to allow for the folding and compacting of the hernia mesh patch for its insertion through the small entrance incision. In respect to all sizes of these hernia mesh patches, the presence of the monofilament fiber spring also allows for the use of a smaller diameter mesh fiber, which might otherwise be necessary to provide the necessary stiffness in a patch not having such a fiber spring.

In respect to large hernia mesh patches, the spring may include the winding of two or more monofilament fibers. Also large hernia mesh patches are initially kept from sliding by using a limited number of anchoring stitches. They are placed without creating tension, without significantly increasing a patient's post-operative discomfort, and without contributing to the strength of the overall surgical repair of the patient's hernia.

Regarding the free outer edges of the respective top and bottom layers of the mesh material, they are slit in radial cuts to create scalloped or fringed edges. The bottom layer flat scalloped edges serve to fill uneven voids in the patient's tissue surface, which helps to minimize any risk of the patient's tissue slipping over this patch and allowing the hernia to recur. The top scalloped edges are folded back and sewn along the monofilament fiber spring, leaving some portions of their folded over scalloped edges free to subsequently resist the migration of this hernia mesh patch, after it has been inserted into the limited sized properitoneal pocket or pouch developed by the surgeon under the patient's hernia defect. The hernia mesh patch held in its intended shape by the fiber spring completely fills enough of this pocket to completely extend over and beyond the patient's hernia defect. After its initial insertion, and thereafter, the patient's hernia mesh patch is held in position by the hydrostatic pressures created between the two tissue layers of fascia above the patch and the peritoneum below the patch.

In respect to all the hernia mesh patches, they have their simplicity of design and method of insertion. They adequately underlay a hernia defect by a minimum of two centimeters around the circumference of the hernia defect, with sufficient rigidity and with sufficient friction to eliminate or minimize sliding or migration. When these hernia mesh patches are used, the repair of inguinal and other abdominal wall hernias are repaired through a smaller wound or incision, with less tension, less post-operative discomfort, shorter operating time, and at a potential lower cost to the patient. The patient's post-operative discomfort is decreased, and risk of any recurrence is likewise decreased.

While the invention has been shown in several embodiments, it should be apparent that it is not limited to those embodiments but is susceptible to various changes without departing from the scope of the invention.

What is claimed is:

1. A method of repair of an abdominal wall hernia, comprising the steps of:
   (a) cutting an incision obliquely positioned above the location described as the internal ring where the hernia has occurred, the cutting extending through the patient's skin, subcutaneous fatty tissues, and the external oblique fascia, which is cut parallel with the fibers thereof a short distance to expose the underlying internal oblique muscle;
   (b) separating portions of the internal oblique muscle to in turn expose the transversalis fascia;
   (c) cutting the transversalis fascia to create an entrance into the preperitoneal space above the peritoneum at a location above the hernia;
   (d) identifying and freeing the hernia sac;
   (e) creating a pocket in the preperitoneal space;
   (f) providing a hernia mesh patch made of a first layer to extend across and beyond a hernia, and a second layer secured to the first layer to create a pouch therebetween, the pouch having an opening for the insertion of a finger of a surgeon, and a resilient support member located in the pouch that creates tension throughout both layers;
   (g) folding and compacting the hernia mesh patch;
   (h) directing the folded and compacted hernia mesh patch down through the incision and beyond into the preperitoneal space;
   (i) expanding the hernia mesh patch in the preperitoneal space by positioning it so the support member freely creates the tension throughout both layers;
   (j) inserting a finger of the surgeon through the incision and beyond to the transverse slit and into the pouch of the hernia mesh patch;
   (k) directing the hernia mesh patch through the preperitoneal space and into the pocket by the hernia;
   (l) withdrawing the finger from the hernia patch and back up through the incision such that the support member remains implanted in the patient; and
   (m) closing the incision with stitches.

2. The method of claim 1 wherein step (a) comprises cutting the incision approximately three centimeters.

3. The method of claim 1 wherein step (a) comprises cutting the incision approximately two to three centimeters above the location described as the internal ring.

4. The method of claim 1 wherein step (f) includes providing holes at spaced locations within the pouch, whereby the friction is increased to insure the hernia mesh patch will remain in place, and whereby subsequently the scar tissue will grow through these spaced holes.

5. The method of claim 1 wherein step (f) includes extending at least one of the layers beyond the pouch, defining a border with a free edge to enhance tissue growth.

6. The method of claim 5 wherein the border is cut at spaced locations to enhance tissue growth.

7. A method of repair of an abdominal wall hernia, comprising the steps of:
   (a) cutting an incision obliquely positioned above the location described as the internal ring, where the hernia has occurred, with this cutting extending through the patient's skin, subcutaneous fatty tissues, and the external oblique fascia, which is cut parallel with the fibers thereof a short distance, exposing the underlying internal oblique muscle;
   (b) separating portions of the internal oblique muscle to in turn expose the transversalis fascia;
   (c) cutting the transversalis fascia creating an entrance into the preperitoneal space above the peritoneum at a location above the hernia;
   (d) identifying and freeing the hernia sac;
   (e) creating a pocket in the preperitoneal space;
   (f) providing a hernia mesh patch made of a first layer to extend across and beyond a hernia, and a second layer secured to the first layer to create a generally planar configuration for the patch joined together by a seam, creating an interior space, serving as a pouch between these first and second layers, and having a transverse slit for the insertion of a finger of a surgeon into the pouch, and having a resilient support member located within the pouch adjacent to the seam for urging the patch to conform to the generally planar configuration;

(g) folding and compacting the hernia mesh patch;

(h) directing the folded and compacted hernia mesh patch down through the incision and beyond into the preperitoneal space;

(i) expanding the hernia mesh patch in the preperitoneal space by positioning it so the support member freely urges the patch to conform to the generally planar configuration;

(j) inserting a finger of the surgeon through the incision and beyond to the transverse slit and into the pouch of the hernia mesh patch;

(k) directing the hernia mesh patch through the preperitoneal space and into the pocket by the hernia;

(l) withdrawing the finger from the hernia patch and back up through the incision such that the support member remains implanted in the patient; and (m) closing the incision with stitches.

8. The method of claim 7 wherein step (a) comprises cutting the incision approximately three centimeters.

9. The method of claim 7 wherein step (a) comprises cutting the incision approximately two to three centimeters above the location described as the internal ring.

10. The method of claim 7 wherein step (a) comprises cutting the incision approximately three centimeters long and approximately two to three centimeters above the location described as the internal ring.

11. The method of claim 7 wherein step (f) includes providing holes at spaced locations within the pouch, whereby the friction is increased to insure the hernia mesh patch will remain in place, and whereby subsequently the scar tissue will grow through these spaced holes.

12. The method of claim 7 wherein step (f) includes extending at least one of the layers beyond the pouch, defining a border with a free edge to enhance tissue growth.

13. The method of claim 12 wherein the border is cut at spaced locations to enhance tissue growth.

14. A method for repairing a tissue aperture, comprising the steps of:

(a) cutting an incision obliquely positioned above the location described as the internal ring where the tissue aperture has occurred, the cutting extending through the patient's skin, subcutaneous fatty tissues, and the external oblique fascia, which is cut parallel with the fibers thereof a short distance to expose the underlying internal oblique muscle;

(b) separating portions of the internal oblique muscle to in turn expose the transversalis fascia;

(c) cutting the transversalis fascia to create an entrance into the preperitoneal space above the peritoneum at a location above the tissue aperture;

(d) identifying and freeing the tissue aperture sac;

(e) creating a pocket in the preperitoneal space;

(f) providing a tissue aperture mesh patch made of a first layer of inert, synthetic mesh material to extend across and beyond a tissue aperture, and a second layer of inert, synthetic mesh material secured to the first layer to create a pouch therebetween, the pouch having an opening for the insertion of a finger of a surgeon, and a resilient support member located in the pouch for creating tension in both of the layers;

(g) folding and compacting the patch;

(h) directing the folded and compacted patch down through the incision and beyond into the preperitoneal space;

(i) expanding the patch in the preperitoneal space by positioning it so the support member freely creates the tension throughout both layers;

(j) inserting a finger of the surgeon through the incision and beyond to the transverse slit and into the pouch of the patch;

(k) directing the patch through the preperitoneal space and into the pocket by the tissue aperture;

(l) withdrawing the finger from the patch and back up through the incision such that the support member remains implanted in the patient; and (m) closing the incision with stitches.

15. The method of claim 14 wherein step (a) comprises cutting the incision approximately three centimeters long and approximately two to three centimeters above the location described as the internal ring.

16. The method of claim 14 wherein step (f) includes providing holes at spaced locations within the pouch, whereby the friction is increased to insure the patch will remain in place, and whereby subsequently the scar tissue will grow through these spaced holes.

17. The method of claim 14 wherein step (f) includes extending at least one of the layers beyond the pouch, defining a border with a free edge to enhance tissue growth.

18. The method of claim 17 wherein the border is cut at spaced locations to enhance tissue growth.

19. A tissue aperture repair patch for implanting within a patient, comprising:

a first layer of insert synthetic mesh material sized and shaped to extend across and beyond a tissue aperture in a patient;

a second layer of insert synthetic mesh material secured to the first layer to create a pouch between the first and second layers;

an opening in the pouch for providing access to an interior of the pouch; and a resilient support member adjacent a periphery of the pouch for urging the layers into a generally planar configuration, the support member being carried by the layers so as to remain implanted with the layer in the patient.

20. The patch according to claim 19, wherein the opening is structured to receive a finger of an individual extending therethrough and into the pouch.

21. The patch according to claim 20, wherein the opening includes a slit extending across at least a portion of one of the first and second layers.

22. The patch according to claim 19, further comprising a plurality of retainers to hold the patch in place after implantation.

23. The patch according to claim 22, wherein each of the plurality of retainers is formed on at least one of the first and second layers.

24. The patch according to claim 23, wherein the plurality of retainers includes a plurality of dart-shaped tabs which protrude from the one of the first and second layers to engage tissue of a patient.

25. The patch according to claim 24, wherein each of the plurality of dart-shaped tabs is defined by a dart-shaped slit in the at least one of the first and second layers.

26. The patch according to claim 19, further comprising a plurality of anchors to hold the patch in place after implantation.

27. The patch according to claim 26, wherein each of the plurality of anchors is disposed on and extends from the support member.

28. The patch according to claim 27, wherein the plurality of anchors includes a plurality of spikes.

29. The patch according to claim 27, wherein the plurality of anchors is integrally formed with the support member.

30. The patch according to claim 19, wherein the support member includes a monofilament fiber.

31. The patch according to claim 19, wherein the first and second layers are secured to each other by a pair of spaced seams extending about the periphery of the pouch, the support member being disposed between the pair of seams.

32. The patch according to claim 19, further comprising a plurality of holes extending through the first and second layers.

33. The patch according to claim 32, wherein the plurality of holes is located adjacent the periphery of the pouch.

34. The patch according to claim 19, further comprising:
a seam extending around the periphery of the pouch; and
a border that extends beyond the seam to fill uneven voids in a patient's tissue.

35. The patch according to claim 34, wherein the border includes a plurality of tab portions disposed about the periphery of the pouch.

36. The patch according to claim 34, wherein the border includes a plurality of slits.

37. The patch according to claim 36, wherein each of the plurality of slits extends inwardly from an outer edge of the border.

38. A tissue aperture repair patch for implanting within a patient, comprising:
a first layer of insert synthetic mesh material sized and shaped to extend across and beyond a tissue aperture in a patient;
a second layer of insert synthetic mesh material overlying the first layer;
the first and second layers being joined together by a seam that defines a pouch between the first and second layers;
an opening in the pouch for providing access to an interior of the pouch to facilitate insertion of the patch into the patient and to position the patch across the tissue aperture; and
a resilient support member located within the pouch adjacent to the seam for urging the patch to conform to a generally flat configuration.

39. The patch according to claim 38, wherein the opening is structured to receive a finger of an individual extending therethrough and into the pouch.

40. The patch according to claim 39, wherein the opening includes a slit extending across at least a portion of one of the first and second layers.

41. The patch according to claim 38, further comprising a border that extends beyond the seam to fill uneven voids in a patient's tissue.

42. The patch according to claim 41, wherein the border includes a plurality of tab portions disposed about the periphery of the pouch.

43. The patch according to claim 41, wherein the border includes a plurality of slits.

44. The patch according to claim 43, wherein each of the plurality of slits extends inwardly from an outer edge of the border.

45. The patch according to claim 38, further comprising a plurality of retainers to hold the patch in place after implantation.

46. The patch according to claim 45, wherein each of the plurality of retainers is formed on at least one of the first and second layers.

47. The patch according to claim 46, wherein the plurality of retainers includes a plurality of dart-shaped tabs which protrude from the one of the first and second layers to engage tissue of a patient.

48. The patch according to claim 47, wherein each of the plurality of dart-shaped tabs is defined by a dart-shaped slit in the at least one of the first and second layers.

49. The patch according to claim 38, further comprising a plurality of anchors to hold the patch in place after implantation.

50. The patch according to claim 49, wherein each of the plurality of anchors is disposed on and extends from the support member.

51. The patch according to claim 50, wherein the plurality of anchors includes a plurality of spikes.

52. The patch according to claim 50, wherein the plurality of anchors is integrally formed with the support member.

53. The patch according to claim 38, wherein the support member includes a monofilament fiber.

54. The patch according to claim 38, further comprising a plurality of holes extending through the first and second layers.

55. The patch according to claim 54 wherein the plurality of holes is located adjacent the periphery of the pouch.

56. A method of repair of an abdominal wall hernia, comprising the steps of:
(a) cutting an incision obliquely positioned above the location described as the internal ring where the hernia has occurred, the cutting extending through the patient's skin, subcutaneous fatty tissues, and the external oblique fascia, which is cut parallel with the fibers thereof a short distance to expose the underlying internal oblique muscle;
(b) separating portions of the internal oblique muscle to in turn expose the transversalis fascia;
(c) cutting the transversalis fascia to create an entrance into the preperitoneal space above the peritoneum at a location above the hernia;
(d) identifying and freeing the hernia sac;
(e) creating a pocket in the preperitoneal space;
(f) obtaining a hernia mesh patch made of a layer of inert synthetic mesh material selectively sized and shaped to extend across and beyond the hernia, the hernia mesh patch having a resilient support member that urges the layer of the inert synthetic mesh material into a generally planar configuration;
(g) folding and compacting the hernia mesh patch;
(h) directing the folded and compacted hernia mesh patch down through the incision and beyond into the preperitoneal space;
(i) expanding the hernia mesh patch in the preperitoneal space by positioning it so the resilient support member moves the layer of the mesh material into the generally planar configuration;

(j) inserting a finger of a surgeon through the incision and
(m) closing the incision with stitches.beyond into engagement with the hernia mesh patch;
(k) directing the hernia mesh patch through the preperitoneal space and into the pocket by the hernia;
(l) withdrawing the surgeon's finger from engagement with the hernia patch and back up through the incision such that the support member remains implanted in the patient; and 57. The method of claim 56 wherein step (a) comprises cutting the incision approximately three centimeters.

58. The method of claim 57 wherein step (a) comprises cutting the incision approximately two to three centimeters above the location described as the internal ring.

\* \* \* \* \*

UNITED STATES PATENT AND TRADEMARK OFFICE
CERTIFICATE OF CORRECTION

PATENT NO. : 6,224,616 B1
DATED : May 1, 2001
INVENTOR(S) : Robert D. Kugel

It is certified that error appears in the above-identified patent and that said Letters Patent is hereby corrected as shown below:

Column 10, claim 19,
Lines 30 and 33, replace "insert" with -- inert --.

Column 11, claim 38,
Lines 31 and 34, replace "insert" with -- inert --.

Column 13, claim 56,
Please rewrite column 13 as follows:

-- (j) inserting a finger of a surgeon through the incision and beyond into engagement with the hernia mesh patch;
    (k) directing the hernia mesh patch through the preperitoneal space and into the pocket by the hernia;
    (l) withdrawing the surgeon's finger from engagement with the hernia mesh patch and back up through the incision such that the support member remains implanted in the patient; and
    (m) closing the incision with stitches. --

Signed and Sealed this

Second Day of April, 2002

*Attest:*

JAMES E. ROGAN
*Attesting Officer*     *Director of the United States Patent and Trademark Office*